(12) United States Patent
Kim et al.

(10) Patent No.: US 9,241,965 B2
(45) Date of Patent: Jan. 26, 2016

(54) **COMPOSITION CONTAINING *PRUNUS MUME* EXTRACT FOR EXTERNAL APPLICATION TO SKIN**

(75) Inventors: Hyuk Kim, Yongin-si (KR); Hyun Ju Koh, Anyang-si (KR); Hong Ju Shin, Seongnam-si (KR); Jeong Hwan Kim, Paju-si (KR); Won Seok Park, Seoul (KR)

(73) Assignee: AMOREPACIFIC CORPORATION (KR)

( * ) Notice: Subject to any disclaimer, the term of this patent is extended or adjusted under 35 U.S.C. 154(b) by 397 days.

(21) Appl. No.: 13/821,710

(22) PCT Filed: Sep. 8, 2011

(86) PCT No.: PCT/KR2011/006670
§ 371 (c)(1),
(2), (4) Date: Mar. 8, 2013

(87) PCT Pub. No.: WO2012/033368
PCT Pub. Date: Mar. 15, 2012

(65) Prior Publication Data
US 2013/0164391 A1    Jun. 27, 2013

(30) Foreign Application Priority Data
Sep. 8, 2010  (KR) .......................... 10-2010-0088082

(51) Int. Cl.
| *A61K 36/00* | (2006.01) |
| *A61K 36/736* | (2006.01) |
| *A61K 36/73* | (2006.01) |
| *A61K 8/97* | (2006.01) |
| *A61Q 19/00* | (2006.01) |

(52) U.S. Cl.
CPC ................. *A61K 36/736* (2013.01); *A61K 8/97* (2013.01); *A61K 36/73* (2013.01); *A61Q 19/00* (2013.01)

(58) Field of Classification Search
None
See application file for complete search history.

(56) References Cited

U.S. PATENT DOCUMENTS

2006/0127429 A1* 6/2006 McCartt et al. ............... 424/401

FOREIGN PATENT DOCUMENTS

| KR | 10-2008-0077762 | 8/2008 |
| KR | 10-2009-0063984 | 6/2009 |
| KR | 100914963 | 8/2009 |
| KR | 10-2010-0000391 | 1/2010 |
| KR | 2010000391 A * | 1/2010 |

OTHER PUBLICATIONS

International Search Report—PCT/KR2011/006670 dated May 1, 2012.
Written Opinion—PCT/KR2011/006670 dated May 1, 2012.

* cited by examiner

*Primary Examiner* — Qiuwen Mi
(74) *Attorney, Agent, or Firm* — Cantor Colburn LLP

(57) ABSTRACT

The present disclosure provides a composition for external application to the skin for skin care after laser treatment, which contains *Prunus mume* extract as an active ingredient. The composition for external application to the skin according to the present disclosure has skin-soothing, skin barrier-recovering and pain-relieving effects and, therefore, can be developed into a cosmetic composition having additional effects of protecting sensitive skin, preventing skin sensitivity, providing skin stability and moisturizing the skin.

5 Claims, 12 Drawing Sheets

| | 1day | 3day |
|---|---|---|
| Vehicle |   |   |
| *Prunus mume* 1% | | |

# COMPOSITION CONTAINING *PRUNUS MUME* EXTRACT FOR EXTERNAL APPLICATION TO SKIN

TECHNICAL FIELD

The present disclosure relates to a composition containing *Prunus mume* extract for external application to the skin.

BACKGROUND ART

Stimulus or heat applied to the skin can cause pain. The transient receptor potential cation channel, subfamily V, member 1 (TRPV1) is a receptor that plays an important role in transmission and modulation of pain. It is mainly found in the nociceptive neurons of the peripheral nervous system (PNS), particularly in the sensory C-fiber and A-fiber neurons. It is also expressed in inflammatory cells, keratinocytes, etc. Well-known activators of TRPV1 include heat higher than 43° C., capsaicin, the pungent compound in hot pepper, acidic condition (low pH), endocannabinoid, anandamide and N-arachidonoyl-dopamine. When activated by these stimulants, TRPV1 acts as an ion channel that allows influx of $Ca^{2+}$ into cells. The $Ca^{2+}$ influx leads to signal transductions causing pain and burning sensation. In addition, it is known that TRPV1 is activated by mitogen-activated protein kinase (MAPK) signaling pathways by nerve growth factor (NGF), bradykinin, prostaglandin 2 (PGE2), tumor necrosis factor-$\alpha$ (TNF-$\alpha$), etc. leading to $Ca^{2+}$ influx into cells.

When the skin temperature is about 42° C., recovery of the skin barrier proceeds slowly. In this case, treatment with the TRPV1 antagonist capsazepine restores the rate of skin barrier recovery to normal level. The heat produced during the laser treatment recently performed by dermatology clinics increases the skin temperature to about 45-50° C. This causes pain, which is thought to be transmitted by the TRPV1 receptor. However, not all the TRPV1 antagonists are effective to relieve the pain caused by the laser treatment.

Accordingly, there is a need of development of a substance among the TRPV1 antagonist that effectively relieves skin irritation or pain and facilitates skin barrier recovery after the laser treatment.

DISCLOSURE

Technical Problem

The present disclosure is directed to providing a composition for external application to the skin for skin care after laser treatment, which has skin-soothing, skin barrier-recovering and pain-relieving effects and further has additional effects of protecting sensitive skin, preventing skin sensitivity, providing skin stability and moisturizing the skin.

Technical Solution

In a general aspect, there is provided a composition for external application to the skin for skin care after laser treatment, which contains *Prunus mume* extract as an active ingredient.

Advantageous Effects

A composition for external application to the skin according to the present disclosure has skin-soothing, skin barrier-recovering and pain-relieving effects and, therefore, can be developed into a cosmetic composition having additional effects of protecting sensitive skin, preventing skin sensitivity, providing skin stability and moisturizing the skin.

BEST MODE

Hereinafter, the present disclosure is described in detail.

In an aspect, the present disclosure provides a composition for external application to the skin for skin care after laser treatment, which contains *Prunus mume* extract as an active ingredient.

The composition may provide skin-soothing, skin barrier-recovering and pain-relieving effects after laser treatment since *Prunus mume* effectively acts as an antagonist of the transient receptor potential cation channel, subfamily V, member 1 (TRPV1).

In an exemplary embodiment of the present disclosure, the composition may contain 0.001-10 wt %, specifically 0.02-5 wt %, of the *Prunus mume* extract based on the total weight of the composition. If the content of the *Prunus mume* extract is less than 0.001%, the desired physiological effect may not be achieved. And, if the content exceeds 10%, skin irritation or solubility problem may occur.

In another aspect, the present disclosure provides a cosmetic composition containing the composition. The cosmetic composition may provide the effects of protecting sensitive skin, preventing skin sensitivity, providing skin stability and moisturizing the skin.

The composition provides the effects of protecting sensitive skin and preventing skin sensitivity by relieving skin irritation and pain after laser treatment. Further, the composition recovers the skin barrier by reducing erythema occurring after laser treatment. The recovered skin barrier provides stability to the skin and moisturizes the skin by preventing loss of water.

The cosmetic composition may be in the form selected from a group consisting of solution, suspension, emulsion, paste, gel, lotion, cream, essence, pack, soothing mask, topical patch, makeup base, moisturizing oil, powder, soap, surfactant-containing cleanser, oil, powder foundation, emulsion foundation, wax foundation, oil-in-water (O/W) or water-in-oil (W/O) emulsion and spray.

<Test Example 1> Calcium influx assay (effect as TRPV antagonist, for pre-treatment)

TRPV1-transfected CHO-VR1 cells were seeded onto a 96-well plate at a density of 80000 cells/well. After incubation at 37° C. for 24 hours, the cells were reacted with Calcium 5 dye for 1 hour. After pre-treating with *Prunus mume, Polygonum multiflorum, Atractylodes macrocephala* or *Phyllostachys nigra* for 10 minutes, RFU value was measured in real time while treating with CAP. The difference between the maximum and minimum RFU values for each condition is graphically represented.

Figure 1:
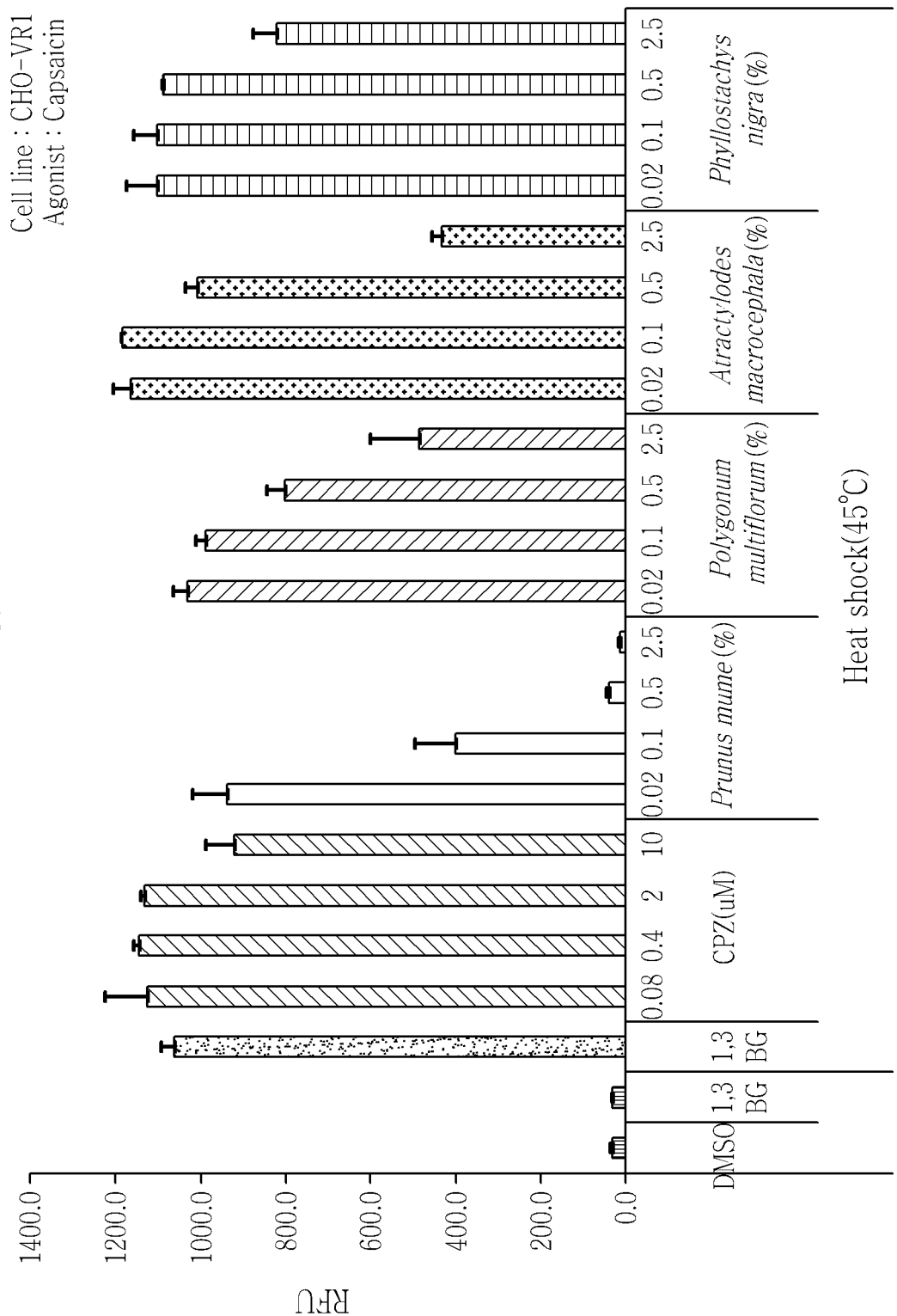
FIG. 1 shows inhibition of calcium influx caused by activation of TRPV1 by capsaicin in TRPV1-transfected CHO-VR1 cells pre-treated with *Prunus mume, Polygonum muftiflorum, Atractylodes macrocephala* and *Phyllostachys nigra*.

FIG. 1 shows inhibition of calcium influx caused by activation of TRPV1 by capsaicin in the TRPV1-transfected CHO-VR1 cells pre-treated with *Prunus mume, Polygonum multiflorum, Atractylodes macrocephala* and *Phyllostachys nigra*. Dimethyl sulfoxide (DMSO) was used as a solvent for capsazepine (CPZ) and 1,3-butylene glycol (1,3-BG) was used as a solvent for *Prunus mume, Polygonum multiflorum, Atractylodes macrocephala* and *Phyllostachys nigra* extracts.

Figure 2:
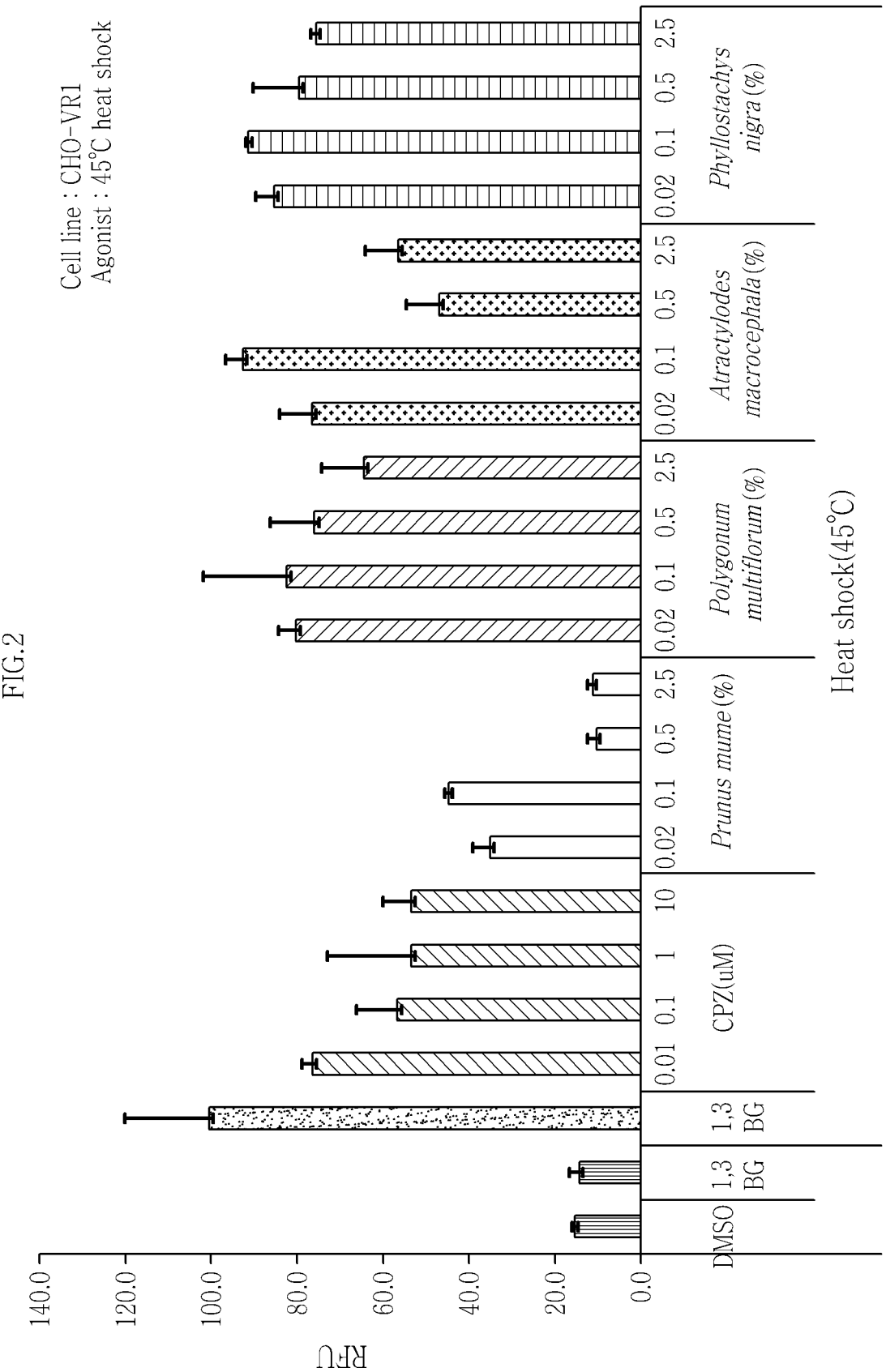
FIG. 2 shows inhibition of calcium influx caused by activation of TRPV1 by heat (45° C.) in TRPV1-transfected CHO-VR1 cells pre-treated with *Prunus mume, Polygonum multiflorum, Atractylodes macrocephala* and *Phyllostachys nigra*.

FIG. 2 shows inhibition of calcium influx caused by activation of TRPV1 by heat (45° C.) in the TRPV1-transfected CHO-VR1 cells pre-treated with *Prunus mume, Polygonum multiflorum, Atractylodes macrocephala* and *Phyllostachys nigra*.

Figure 3:
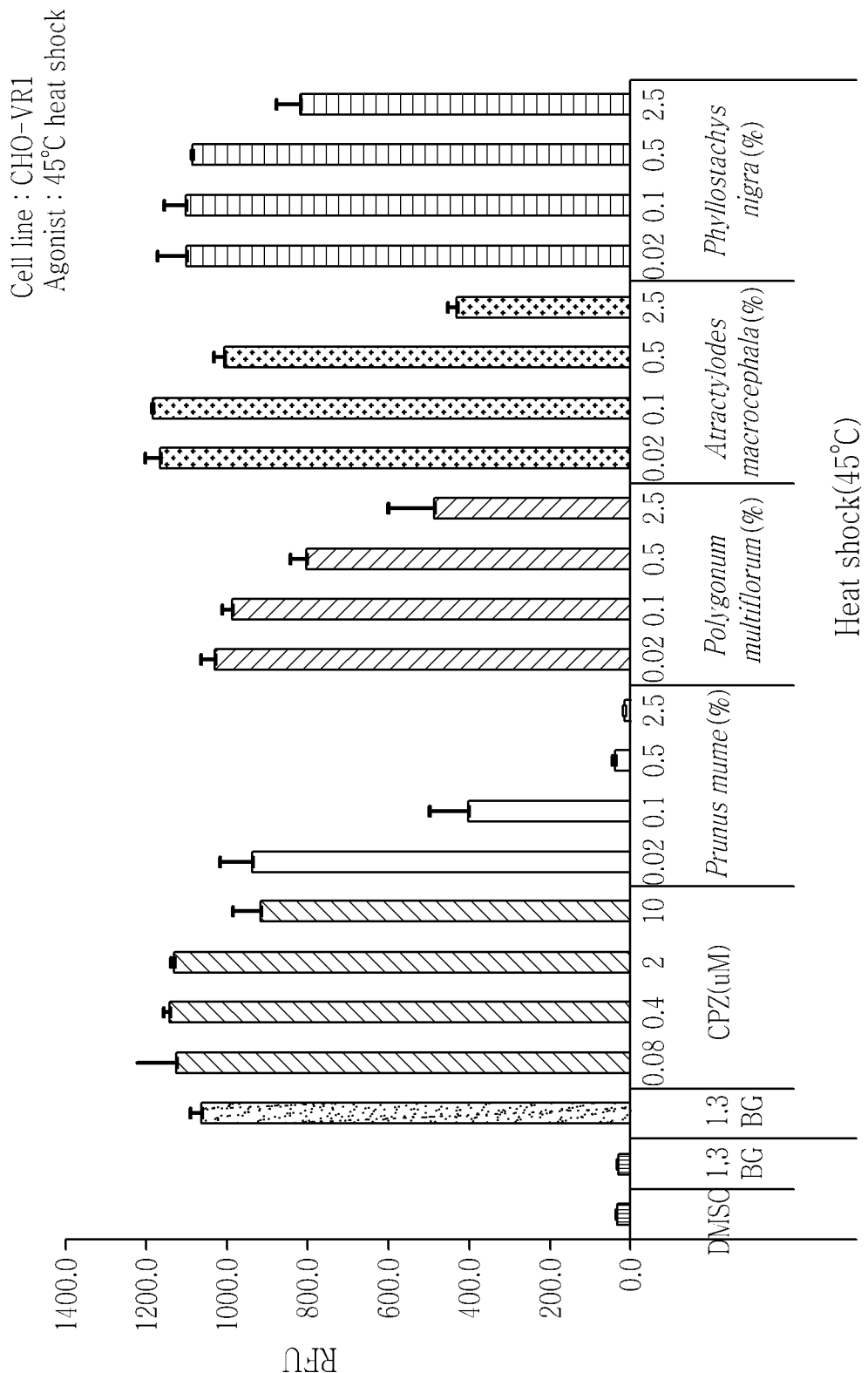
FIG. 3 shows inhibition of calcium influx caused by activation of TRPV1 by heat (45° C.) in TRPV1-transfected keratinocytes (HaCAT cells) pre-treated with *Prunus mume, Polygonum multiflorum, Atractylodes macrocephala* and *Phyllostachys nigra*.

And, FIG. 3 shows inhibition of calcium influx caused by activation of TRPV1 by heat (45° C.) in TRPV1-transfected keratinocytes (HaCAT cells) pre-treated with *Prunus mume, Polygonum multiflorum, Atractylodes macrocephala* and *Phyllostachys nigra*.

As seen from FIGS. 1-3, calcium influx induced by capsaicin and deionized water (DW) of 45° C. was inhibited in the order of *Prunus mume*>*Atractylodes macrocephala*>*Polygonum multiflorum*.

<Test Example 2> Calcium influx assay (effect as TRPV antagonist, for post-treatment)

Figure 4:
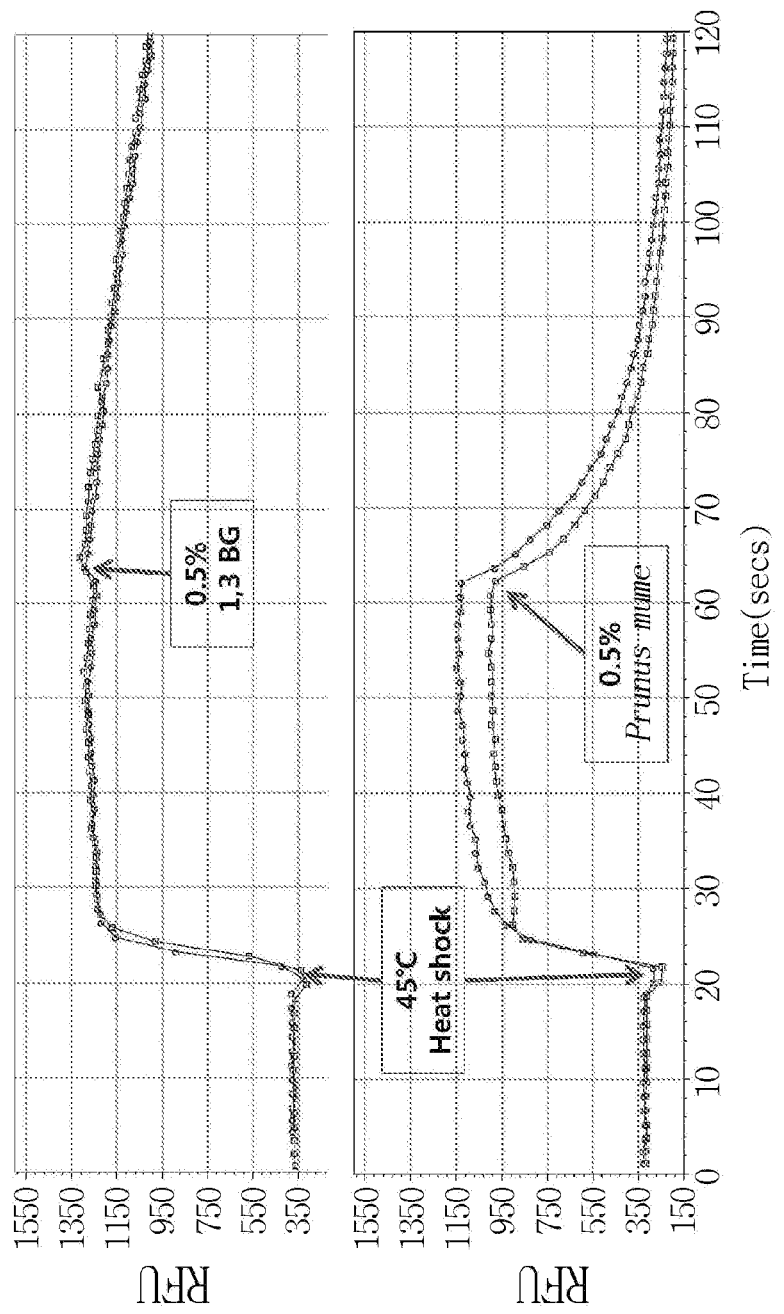
FIG. 4 shows inhibition of calcium influx caused by activation of TRPV1 by heat (45° C.) in HaCAT cells post-treated with 1,3-butylene glycol (1,3-BG) or 0.5% *Prunus mume* extract.
Figure 5:
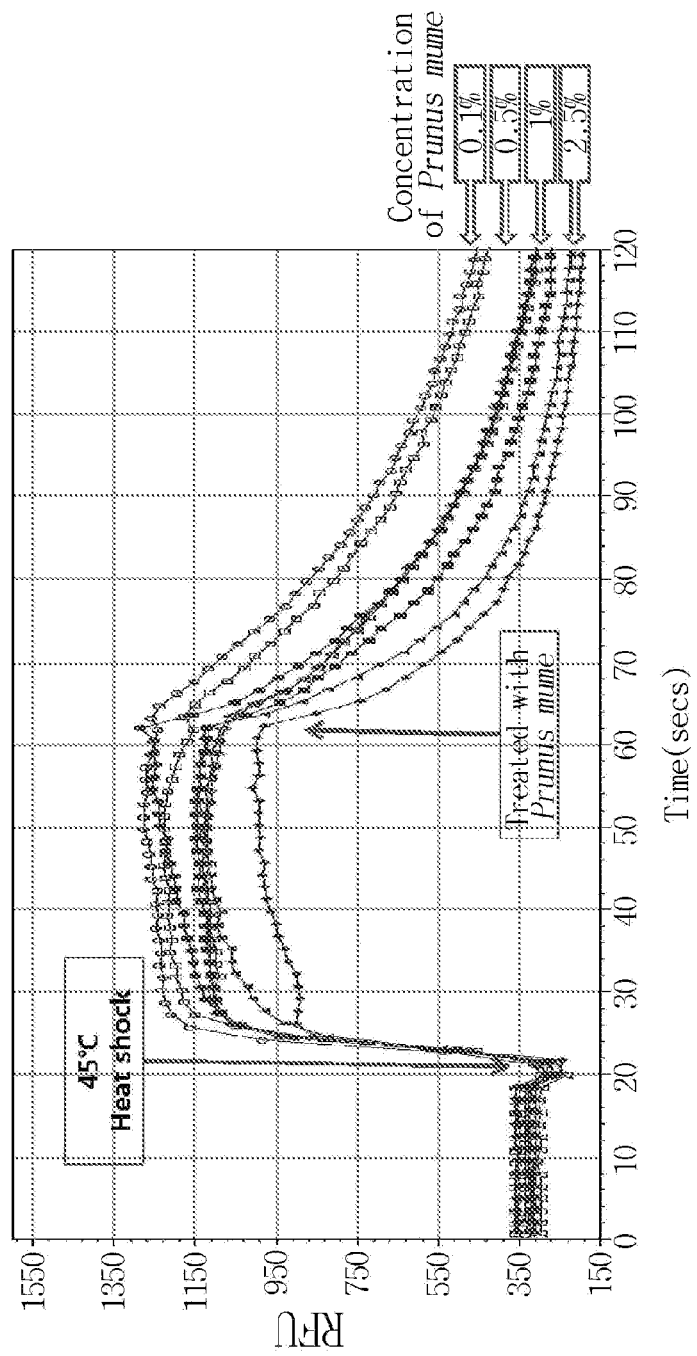
FIG. 5 shows inhibition of calcium influx caused by activation of TRPV1 by heat (45° C.) in HaCAT cells post-treated with *Prunus mume* extract of various concentrations.

HaCAT cells were treated with DW of 45° C. to increase calcium influx. Then, after post-treating with *Prunus mume, Polygonum multiflorum* or *Atractylodes macrocephala*, inhibition of calcium influx was measured. The difference between the maximum and minimum RFU values for each condition is graphically represented. FIG. 4 shows inhibition of calcium influx caused by activation of TRPV1 by heat (45° C.) in the HaCAT cells post-treated with 1,3-butylene glycol (1,3-BG) or 0.5% *Prunus mume* extract. It can be seen that the *Prunus mume* extract inhibits calcium influx. FIG. 5 shows that calcium influx induced by heat (45° C.) is inhibited in the HaCAT cells post-treated with the *Prunus mume* extract of various concentrations.

Figure 6:
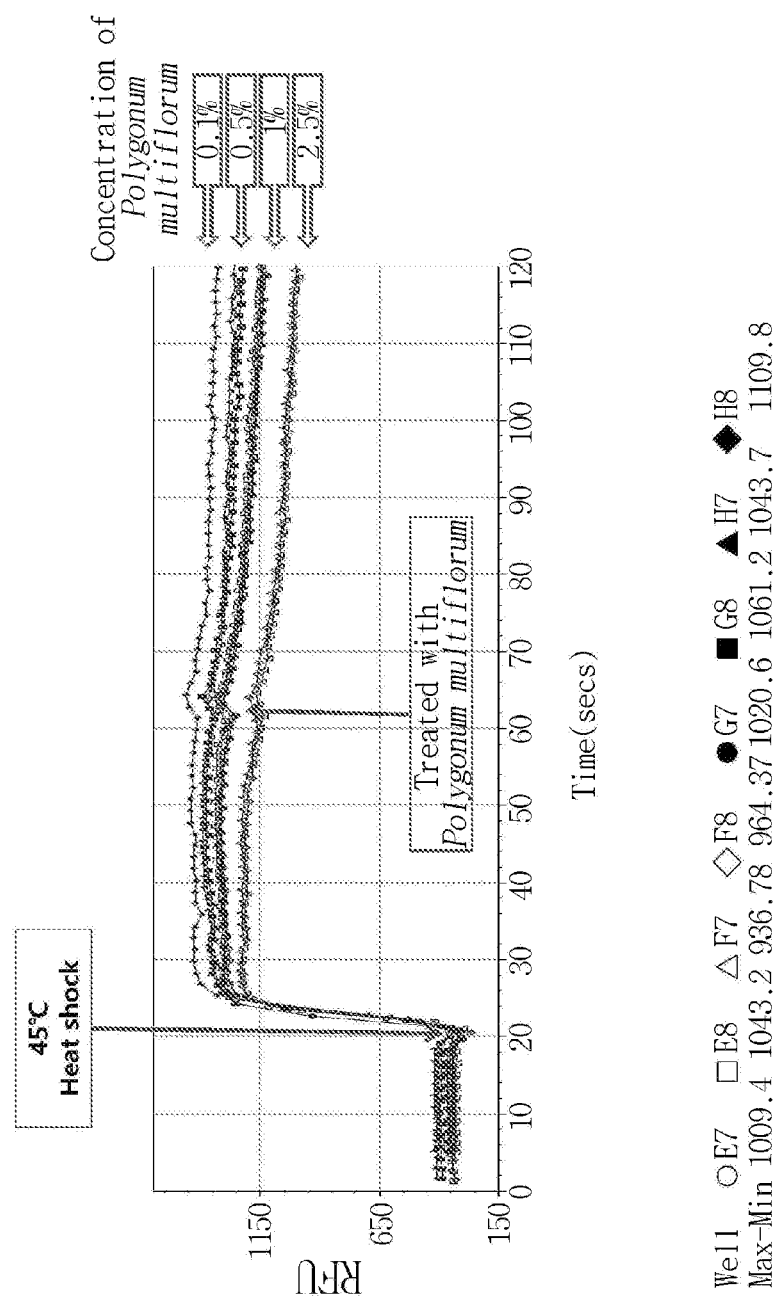
FIG. 6 shows inhibition of calcium influx caused by activation of TRPV1 by heat (45° C.) in HaCAT cells post-treated with *Polygonum multiflorum* extract of various concentrations.
Figure 7:
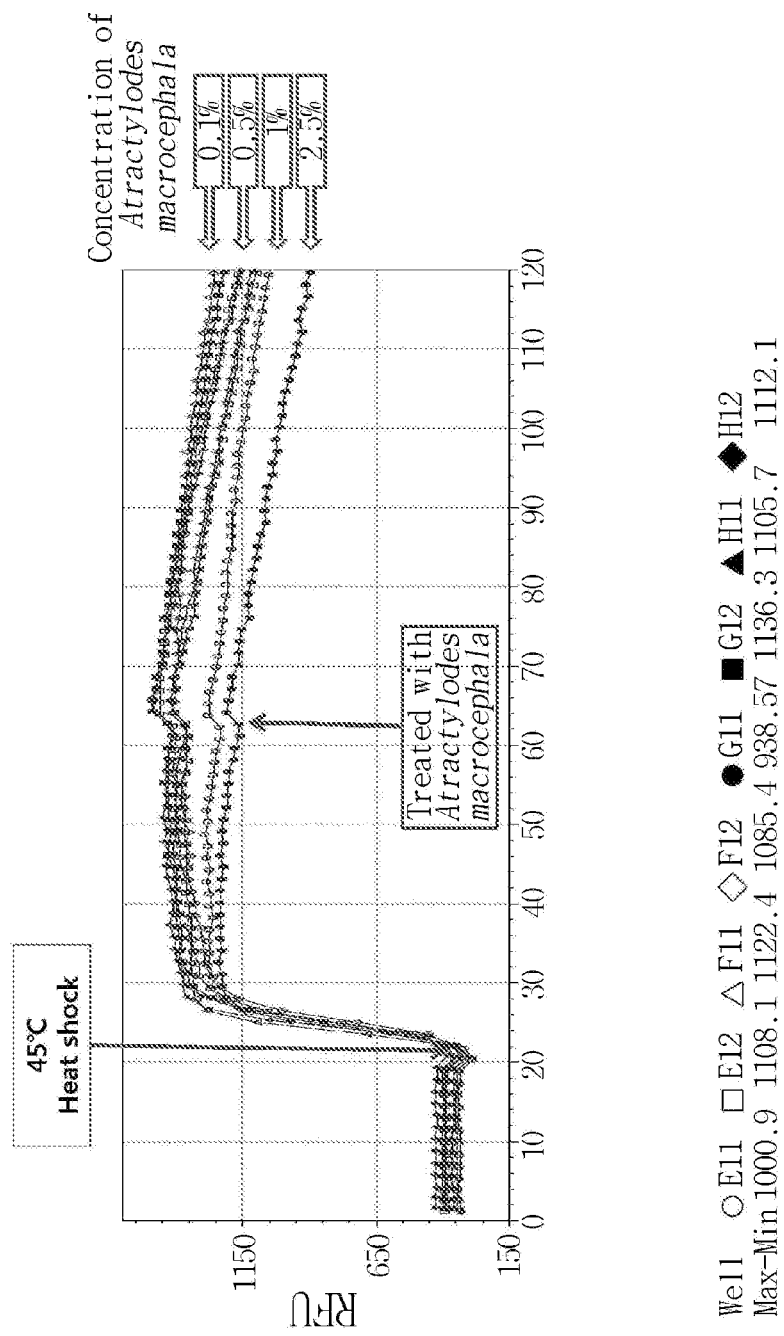
FIG. 7 shows inhibition of calcium influx caused by activation of TRPV1 by heat (45° C.) in HaCAT cells post-treated with *Atractylodes macrocephala* extract of various concentrations.

FIG. 6 shows inhibition of calcium influx caused by activation of TRPV1 by heat (45° C.) in the HaCAT cells post-treated with *Polygonum multiflorum* extract of various concentrations and FIG. 7 shows inhibition of calcium influx caused by activation of TRPV1 by heat (45° C.) in the HaCAT cells post-treated with *Atractylodes macrocephala* extract of various concentrations. As seen from FIG. 6 and FIG. 7, post-treatment with the *Polygonum multiflorum* extract and the *Atractylodes macrocephala* extract after heat stimulation was not effective for inhibiting calcium influx, unlike Test Example 1. Accordingly, it was first identified that, for post-treatment after laser treatment, only *Prunus mume* is effective as the TRPV1 antagonist.

<Test Example 3> Inhibition of erythema in mice

Three hairless mice were irradiated with fractional $CO_2$ laser (tip type 120 mm, pulse energy 60 mJ, density 200 spots/cm$^2$, scan type 8 mm) at two sites per mouse. On days 0, 1, 2 and 3, 20 µL of test sample was applied and Tegaderm was attached on the irradiation sites, which was removed the next day. On days 1 and 3, transepidermal water loss (TEWL) was measured using VapoMeter (Delfin, Finland) and L-value and a-value were measured using Chroma Meter (Minolta, Japan). Also, visual inspection was performed.

Figure 8:
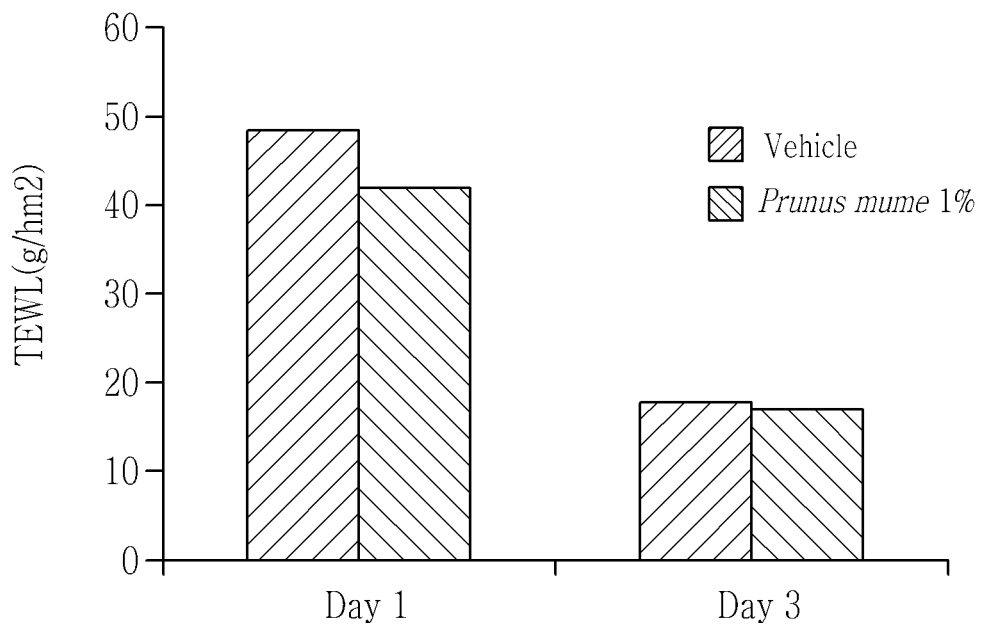
FIG. 8 shows a result of measuring transepidermal water loss (TEWL) after irradiating fractional $CO_2$ laser to hairless mice and post-treating with *Prunus mume* extract.
Figure 9:
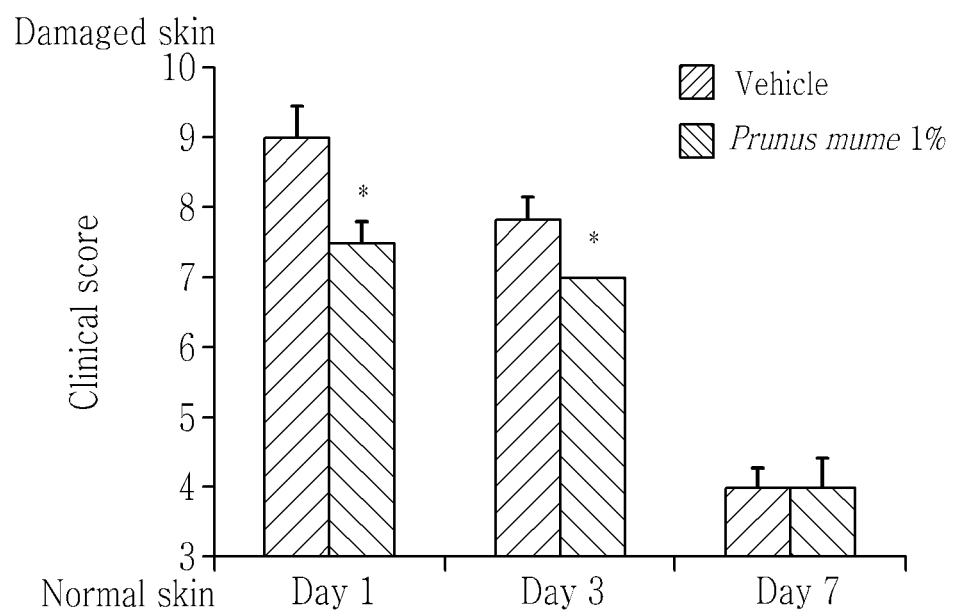
FIG. 9 shows a result of measuring clinical scores after irradiating fractional $CO_2$ laser to hairless mice and post-treating with *Prunus mume* extract.
Figure 10:
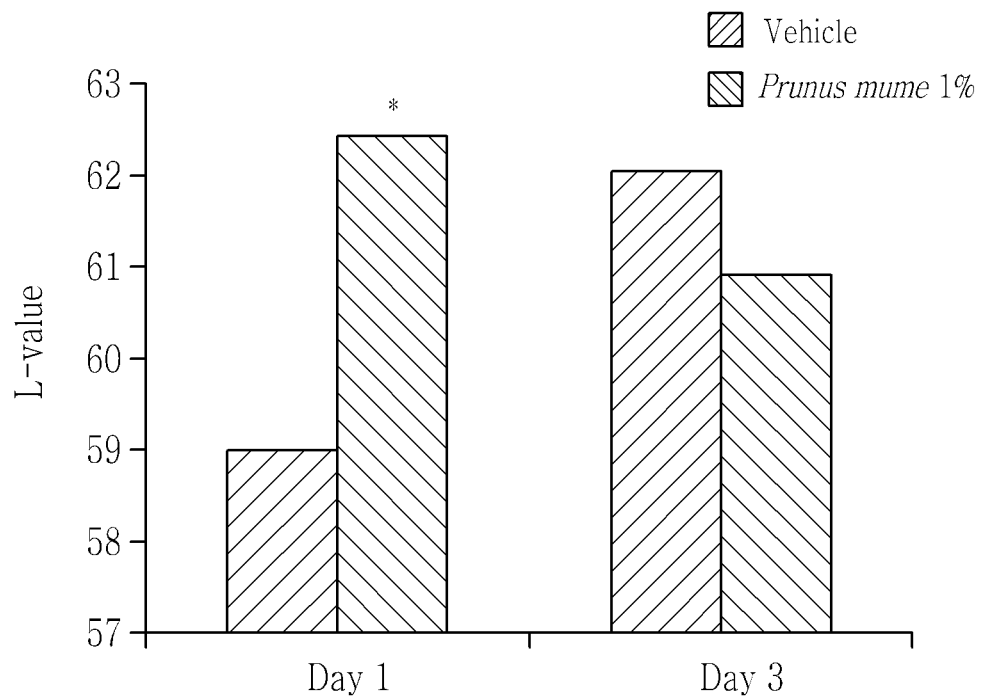
FIG. 10 shows a result of measuring L-values after irradiating fractional $CO_2$ laser to hairless mice and post-treating with *Prunus mume* extract.
Figure 11:
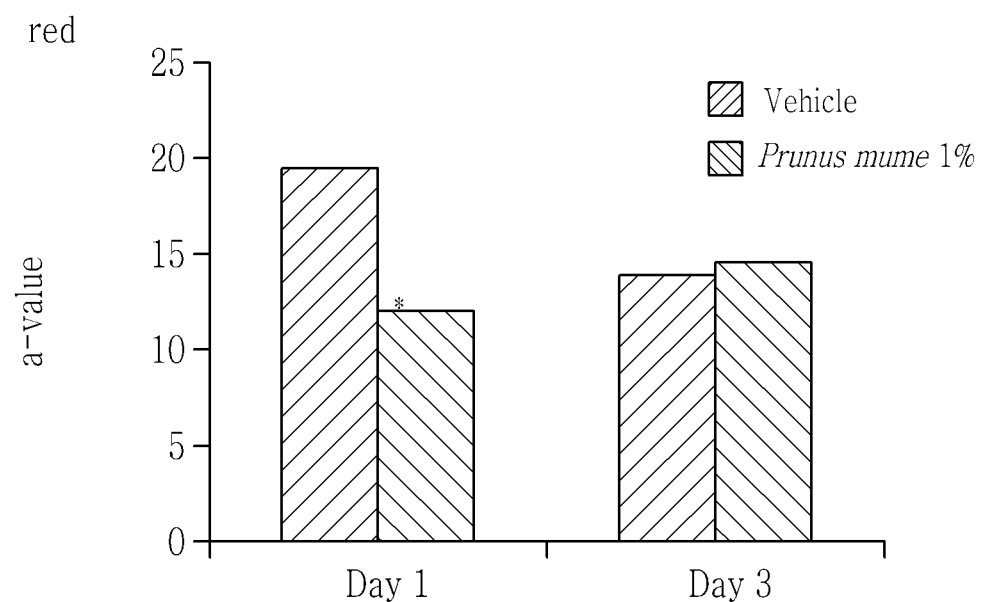
FIG. 11 shows a result of measuring a-values after irradiating fractional $CO_2$ laser to hairless mice and post-treating with *Prunus mume* extract.
Figure 12:
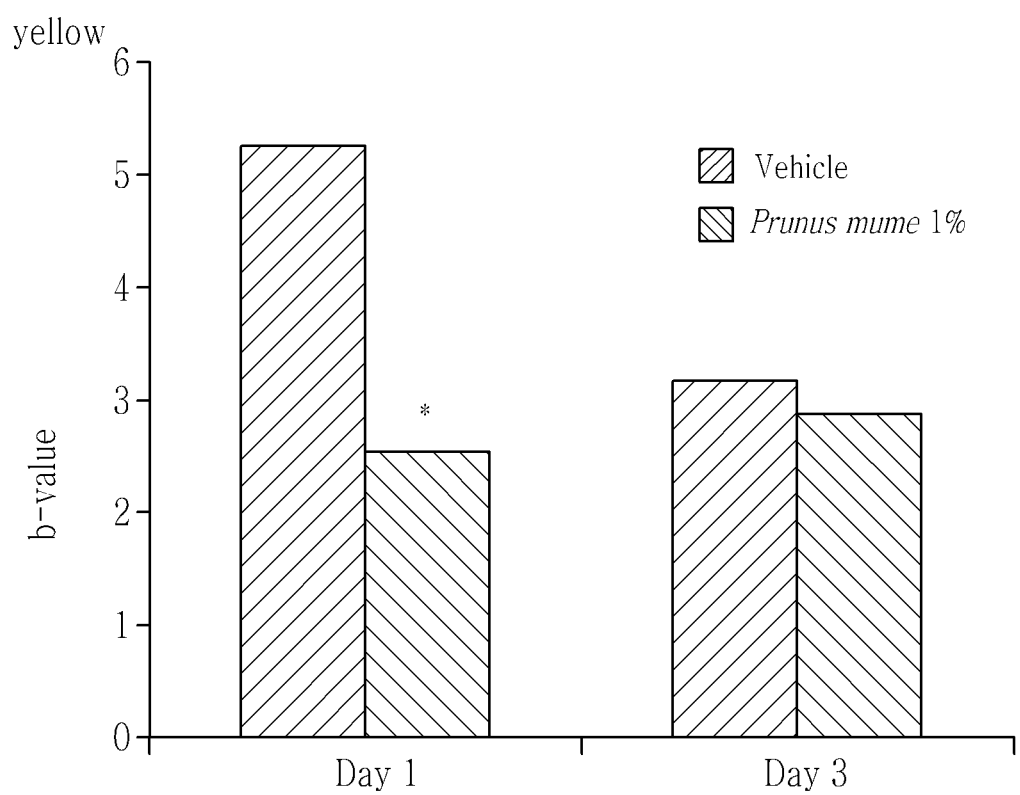
FIG. 12 shows a result of measuring b-values after irradiating fractional $CO_2$ laser to hairless mice and post-treating with *Prunus mume* extract.
Figure 13:
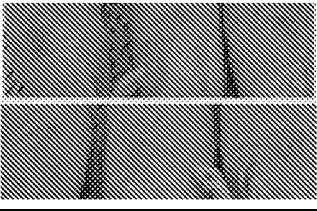
FIG. 13 shows a visual inspection result after irradiating fractional $CO_2$ laser to hairless mice and post-treating with *Prunus mume* extract.
Figure 13:
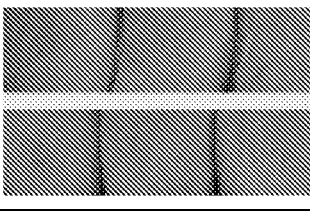
Figure 13:
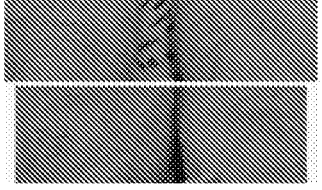
Figure 13:
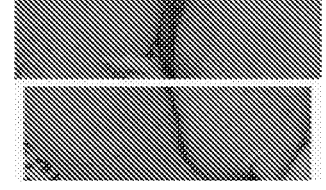

TEWL measurement result is shown in FIG. 8, clinical scores in FIG. 9, L-values in FIG. 10, a-values in FIG. 11, b-values in FIG. 12, and visual inspection result in FIG. 13.

*Prunus mume* showed the effect of inhibiting erythema. Although no significant effect of reducing TEWL was observed, the effect of inhibiting erythema was observed from the visual inspection. Accordingly, it can be seen that *Prunus mume* can prevent loss of water from the skin by reducing erythema occurring after laser treatment and recovering the skin barrier.

<Test Example 4> Relieving of skin pain

Figure 14:
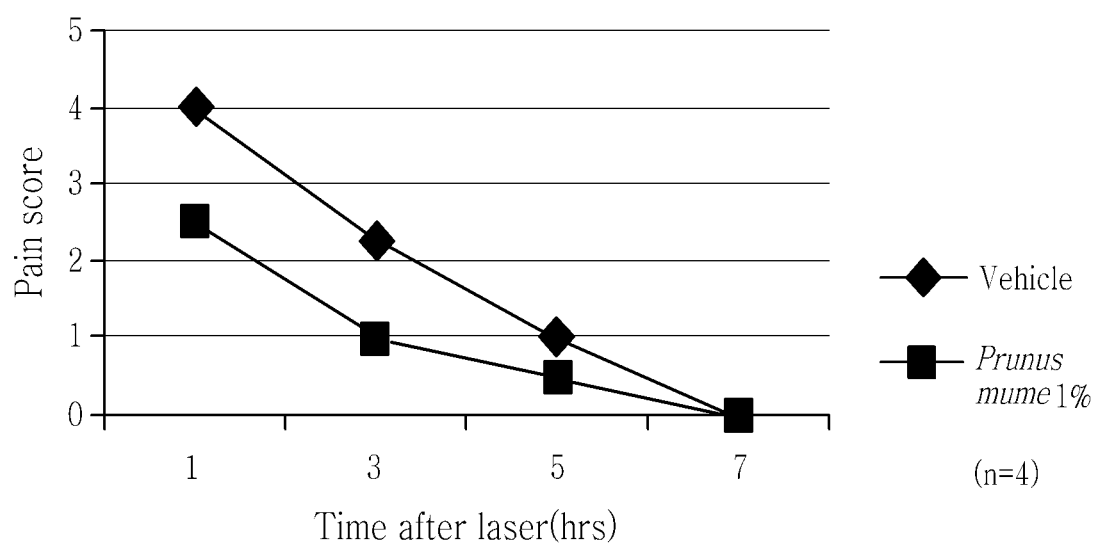
FIG. 14 shows a result of measuring pain scores after irradiating Fraxel laser to human arms and applying test substances.

Fraxel laser (e$CO_2$, Lutronic; pulse energy 80 mJ, density 100 spots/cm$^2$, scan type 12 mm, tip type 120 m) was irradiated to both arms of subjects (n=4) (m). Then, test substance (100 µL) was applied and Tegaderm was attached on the irradiation sites. Pain was evaluated (scores 0-10; 0: no pain, 10: very severe pain) immediately after the irradiation and 1, 3, 5, 7 and 19 hours after the irradiation. The result is shown in FIG. 14.

The result for one subject, for whom *Prunus mume* had no effect 1 hour later but resulted in better pain-relieving effect than the vehicle 3 hours later, was excluded from the data. For the other 3 subjects, *Prunus mume* resulted in excellent effect of relieving pain. *Prunus mume* resulted in pain-relieving effect in both cases where an anesthetic cream (EMLA) was pre-treated before the laser irradiation or not.

Formulation examples of a cosmetic composition and a pharmaceutical composition according to the present disclosure are described below. However, the following examples are for illustrative purposes only and the scope of the present disclosure is not limited by the examples.

[Formulation Example 1] Emollient Lotion (skin lotion)

An emollient lotion was prepared with the composition described in Table 1 according to a commonly employed method.

TABLE 1

| Ingredients | Contents (wt %) |
|---|---|
| *Prunus mume* extract | 1.0 |
| Glycerin | 3.5 |
| Oleyl alcohol | 1.5 |
| Ethanol | 5.5 |
| Polysorbate 80 | 3.2 |
| Carboxyvinyl polymer | 1.0 |
| Butylene glycol | 2.0 |
| Propylene glycol | 2.0 |
| Antiseptic and fragrance | adequate |
| Purified water | balance |
| Total | 100 |

[Formulation Example 2] Nourishing lotion (milk lotion)

A nourishing lotion was prepared with the composition described in Table 2 according to a commonly employed method.

TABLE 2

| Ingredients | Contents (wt %) |
|---|---|
| *Prunus mume* extract | 1.0 |
| Glycerin | 3.0 |
| Butylene glycol | 3.0 |
| Propylene glycol | 3.0 |
| Carboxyvinyl polymer | 0.1 |
| Beeswax | 4.0 |
| Polysorbate 60 | 1.5 |
| Caprylic/capric triglyceride | 5.0 |
| Squalane | 5.0 |
| Sorbitan sesquioleate | 1.5 |
| Cetearyl alcohol | 1.0 |
| Triethanolamine | 0.2 |
| Antiseptic and fragrance | adequate |
| Purified water | balance |
| Total | 100 |

[Formulation Example 3] Nourishing cream

A nourishing cream was prepared with the composition described in Table 3 according to a commonly employed method.

TABLE 3

| Ingredients | Contents (wt %) |
|---|---|
| *Prunus mume* extract | 1.0 |
| Glycerin | 3.5 |
| Butylene glycol | 3.0 |
| Liquid paraffin | 7.0 |
| β-Glucan | 7.0 |
| Carbomer | 0.1 |
| Caprylic/capric triglyceride | 3.0 |
| Squalane | 5.0 |
| Cetearyl glucoside | 1.5 |
| Sorbitan stearate | 0.4 |
| Polysorbate 60 | 1.2 |
| Triethanolamine | 0.1 |
| Antiseptic and fragrance | adequate |
| Purified water | balance |
| Total | 100 |

[Formulation Example 4] Massage cream

A massage cream was prepared with the composition described in Table 4 according to a commonly employed method.

TABLE 4

| Ingredients | Contents (wt %) |
|---|---|
| *Prunus mume* extract | 1.0 |
| Glycerin | 8.0 |
| Butylene glycol | 3.0 |
| Liquid paraffin | 45.0 |
| β-Glucan | 7.0 |
| Carbomer | 0.1 |
| Caprylic/capric triglyceride | 3.0 |
| Beeswax | 4.0 |
| Cetearyl glucoside | 1.5 |
| Sorbitan sesquioleate | 0.9 |
| Paraffin | 1.5 |
| Antiseptic, pigment and fragrance | adequate |
| Purified water | balance |
| Total | 100 |

[Formulation Example 5] Pack

A pack was prepared with the composition described in Table 5 according to a commonly employed method.

TABLE 5

| Ingredients | Contents (wt %) |
|---|---|
| *Prunus mume* extract | 1.0 |
| Glycerin | 4.0 |
| Polyvinyl alcohol | 15.0 |
| Hyaluronic acid extract | 5.0 |
| β-Glucan | 7.0 |
| Allantoin | 0.1 |
| Nonyl phenyl ether | 0.4 |
| Polysorbate 60 | 1.2 |
| Ethanol | adequate |
| Antiseptic and fragrance | adequate |
| Purified water | balance |
| Total | 100 |

[Formulation Example 6] Patch

A patch was prepared with the composition described in Table 6 according to a commonly employed method.

TABLE 6

| Ingredients | Contents (wt %) |
|---|---|
| *Prunus mume* extract | 1.0 |
| β-1,3-Glucan | 3.0 |
| Diethylamine | 0.7 |
| Sodium sulfite | 0.1 |
| Polyoxyethylene lauryl ether (E.O = 9) | 1.0 |
| Polyhydroxyethylene cetyl stearyl ether (Cetomacrogol 1000) | 1.0 |
| Viscous paraffin oil | 2.5 |
| Caprylic/capric ester (Cetiol LC) | 2.5 |
| PEG 400 | 3.0 |
| Polyacrylic acid (Carbopol 934P) | 1.0 |
| Purified water | balance |
| Total | 100 |

While the exemplary embodiments have been shown and described, it will be understood by those skilled in the art that various changes in form and details may be made thereto without departing from the spirit and scope of this disclosure as defined by the appended claims.

In addition, many modifications can be made to adapt a particular situation or material to the teachings of this disclosure without departing from the essential scope thereof. Therefore, it is intended that this disclosure not be limited to the particular exemplary embodiments disclosed as the best mode contemplated for carrying out this disclosure, but that this disclosure will include all embodiments falling within the scope of the appended claims.

The invention claimed is:

1. A method for aftercaring a skin after laser treatment to the skin in a subject, comprising transdermally administering an effective amount of *Prunus mume* extract to the subject after laser treatment to skin, wherein a temperature of the skin is higher than or equal to 45° C.

2. The method according to claim 1, wherein the *Prunus mume* extract soothing soothes the skin, relieves skin pain or recovers the skin barrier.

3. The method according to claim 1, wherein the *Prunus mume* extract is administered in a form of a composition comprising 0.001-10 wt % of the *Prunus mume* extract based on the total weight of the composition.

4. The method according to claim 3, wherein the composition is in the form selected from a group consisting of solution, suspension, emulsion, paste, gel, lotion, cream, essence, pack, soothing mask, topical patch, makeup base, moisturizing oil, powder, soap, surfactant-containing cleanser, oil, powder foundation, emulsion foundation, wax foundation, oil-in-water (O/W) or water-in-oil (W/O) emulsion and spray.

5. The method according to claim 1, wherein the *Prunus mume* extract protects sensitive skin, prevents skin sensitivity, provides skin stability and moisturizes the skin after laser treatment.

* * * * *